(12) United States Patent
Pykett et al.

(10) Patent No.: US 7,195,787 B1
(45) Date of Patent: Mar. 27, 2007

(54) SKINCARE COMPOSITION AGAINST FREE RADICALS

(75) Inventors: Melanie Ann Pykett, Nottingham (GB); Ailsa Helen Craig, Nottingham (GB); Edward Galley, Nottingham (GB); Christopher Smith, Nottingham (GB); Stewart Paul Long, Nottingham (GB)

(73) Assignee: The Boots Company PLC, Nottinghamshire (GB)

( * ) Notice: Subject to any disclaimer, the term of this patent is extended or adjusted under 35 U.S.C. 154(b) by 0 days.

(21) Appl. No.: 10/069,975

(22) PCT Filed: Sep. 7, 2000

(86) PCT No.: PCT/EP00/08729

§ 371 (c)(1),
(2), (4) Date: Oct. 10, 2002

(87) PCT Pub. No.: WO01/17495

PCT Pub. Date: Mar. 15, 2001

(30) Foreign Application Priority Data

Sep. 9, 1999 (GB) .................. 9921238.3

(51) Int. Cl.
*A61K 36/258* (2006.01)
*A61K 36/00* (2006.01)

(52) U.S. Cl. ............. 424/728; 424/725; 424/752; 424/768

(58) Field of Classification Search ........... 424/725, 424/728, 736, 752, 758, 766, 776, 773
See application file for complete search history.

(56) References Cited

U.S. PATENT DOCUMENTS

| 5,084,289 | A | | 1/1992 | Shin et al. |
| 5,164,182 | A | * | 11/1992 | Meybeck et al. ........... 424/773 |
| 5,314,686 | A | | 5/1994 | Todd, Jr. |
| 5,658,578 | A | * | 8/1997 | Ogawa et al. .............. 424/401 |
| 6,066,327 | A | * | 5/2000 | Gubernick et al. ......... 424/401 |
| 6,326,202 | B1 | * | 12/2001 | Mathur et al. .............. 435/410 |
| 6,524,626 | B2 | * | 2/2003 | Chen ........................... 424/728 |

FOREIGN PATENT DOCUMENTS

| WO | WO 98/33494 | 8/1998 |
| WO | WO 99/33439 | 7/1999 |
| WO | WO 00/64278 | 11/2000 |

OTHER PUBLICATIONS

Database WPI, Section Ch, Week 199840, Derwent Publications Ltd., London, GB; AN 1998-463113 XP002156754, "Antioxidant—contains rosemary extract, tocopherol concentrate and higher fatty acid ascorbate", & JP 10 195434 (Lion Corp), Jul. 28, 1998 abstract.

* cited by examiner

*Primary Examiner*—Sreeni Padmanabhan
*Assistant Examiner*—Gina C. Yu
(74) *Attorney, Agent, or Firm*—Rothwell, Figg, Ernst & Manbeck

(57) ABSTRACT

Topical cosmetic compositions for application to the skin comprises a suitable diluent or carrier in combination with a synergistic mixture of three anti-free-radical agents selected from ascorbic acid, its salts, esters, glucosides and glucosamines; tocopherol and its esters; herbal extracts selected from gingko biloba, morus alba, origanum vulgare, panax ginseng, rosmarinus officinalis, birch extract, camellia sinensis, acerola cherry powder and grape seed oil.

5 Claims, No Drawings

SKINCARE COMPOSITION AGAINST FREE RADICALS

The present invention relates to skincare compositions providing enhanced protection for the skin against free-radicals.

As we age, our skin undergoes changes such as becoming thinner, more easily damaged and less elastic. In addition, lifetime exposure to UVA and UVB radiation, together with other environmental pollution from traffic fumes, ozone, cigarette smoke etc, cause additional changes to the skin. These changes, such as lines and wrinkling, actinic lentigines, dyspigmentation, rough skin, actinic telangiectasia and further loss of skin elastic function are due to direct UV mediated damage to cells and indirectly mediated damage caused by the generation of free radicals in cells and tissues. This is generally termed photoageing and can account for up to 90% of the skin changes we associate with ageing.

Due to the major impact photoageing has on skin appearance and function, there has been much research conducted to develop technologies which can prevent the effects and help to repair existing damage.

To prevent sunlight mediated damage of skin cells and associated damage due to sunlight initiating the formation of free radicals in the skin, compositions containing a sunscreen may be used. These compositions generally contain an inorganic sunscreen such as titanium dioxide which reflects the sun's rays, or one or more of an organic sunscreen which absorbs the rays. A further measure to protect the skin is to use compositions containing antioxidants which act as free radical quenchers. These react with the free radicals and so terminate the chain of reactions that free radicals customarily propagate which so damage the skin.

Compositions containing sunscreens are known. Some sunscreen formulations also contain antioxidants. There are also cosmetic compositions, not containing sunscreens, which contain antioxidants for additional skin care and protection.

There are a number of skincare compositions, commercially available, which seek to minimise the damage to the skin by the inclusion of certain agents. In particular materials such as vitamins and herbal extracts have widely been known to reduce the formation of free-radicals. However to achieve good efficiency high levels of these materials have to be used and this can result in dark aesthetically unpleasing products.

The skincare compositions of the present invention have been shown to protect the skin more effectively from free radicals and are cosmetically and aesthetically more suitable than known skin care compositions. Therefore the skincare compositions of the present invention may be used to provide improved protection against damage to skin caused by exposure to factors such as sunlight, environmental and/or atmospheric pollution.

Therefore broadly according to the present invention there is provided a cosmetic composition suitable for application to the skin containing a combination of antioxidant ingredients that when combined together give a synergistic improvement in activity allowing improved protection to be provided for the skin without the drawback of aesthetically unpleasant product appearance.

The present invention provides cosmetic compositions suitable for application to the skin containing a synergistic mixture of three antioxidants in combination with a cosmetically acceptable diluent or carrier. The antioxidant agents used in the present invention are already known for their ability to quench free radicals and prevent oxidative damage to the skin. However the present invention discloses that certain combinations of these agents have a greater efficacy than that expected. This has been demonstrated by both in vivo and in vitro testing.

Suitable antioxidant agents may include:

a) ascorbic acid its salts, esters, glucosides and glucosamines, particularly sodium ascorbyl phosphate, magnesium ascorbyl phosphate and ascorbyl palmitate
b) vitamin E (tocopherol) and its esters, particularly tocopheryl acetate
c) herbal extracts, particularly gingko biloba, such as that available under the trade name "Gingko Biloba Leaf Powder" from Univar PLC, morus alba, such as that available under the trade name "Mulberry Concentrate" from Aston Chemicals, origanum vulgare, such as that available under the trade name "Pronalen Origanum HSC" from S Black Ltd, panax ginseng, such as that available under the trade name "Panax ginseng 1.1 extract 4294" from Black Ltd or "Phytexcell Panax ginseng" available from Croda Chemicals Ltd, birch extract such as those available from Cosmetochem (U.K.) Ltd under the trade names "Super Herbasol Extract Birch" and "HP Herbasol Betula" and those available from Blagden Chemicals under the tradenames "Phytelene of Birch" and "Aqueous Spray Dried Birch", camellia sinensis, such as that available under the trade name "Herbal Extract Green Tea 75% Solids" from Nichimen Europe, rosmarrinus officinalis such as that available under the trade name "Pronalen Rosemary" from S. Black, Acerola cherry powder such as that available as Acerola PE from Gee Lawson and Grape Seed oil such as that available from Chesham Chemicals Limited.

The source of the antioxidant activity in some of these products is often not fully understood; for example, it is believed that the antioxidant activity of ginkgo biloba extract arises from the presence of flavonglycocides and/or terpenelactones which may be free-radical inhibitors. Birch extract may be produced by extracting the dried leaves of Betula alba with a suitable solvent. It is believed that the anti-free radical activity of birch extract arises due to the presence of flavonoids such as hyperosid, quencitrosid and/or myricetol-3-digalactosid which may be free-radical inhibitors. Such products are then often sold as mixtures or solutions.

Thus the antioxidant agent may consist of a number of active ingredients which are free-radical inhibitors or may also comprise suitable diluents and/or carriers (such as when the anti-free radical agent is some of the products mentioned herein). Thus there may be some confusion as to the actual level of agent within a commercially available product. Accordingly, the amounts of antioxidant agents used in the present invention are expressed as dry weights, as understood by a man skilled in the art.

The total amount of antioxidant agents present in the composition may range from 0.005% to 10% by weight, preferably 0.5% to 5%, most preferably 1% to 3.5% by weight of the composition.

Particularly preferred synergistic combinations of antioxidant agents suitable for inclusion in a skin care composition of the present invention are:

panax, ginseng, morus alba and magnesium ascorbyl phosphate;

panax ginseng, morus alba and sodium ascorbyl phosphate;

panax ginseng, morus alba and rosmarinus officinalis;

panax ginseng, morus alba and origanum vulgare.

In these preferred combinations (a) the panax ginseng is preferably present in an amount of 0.005 to 0.1%, more preferably 0.01 to 0.05%, most preferably about 0.03% by weight of the composition; (b) the morus alba is preferably present in an amount of 0.0005 to 0.01 %, more preferably 0.001 to 0.005%, most preferably about 0.0023% by weight of the composition; (c) the sodium or magnesium ascorbyl phosphate is preferably present in an amount of 0.05 to 2.5%, preferably 0.1 to 2%, most preferably 0.15 to 1.5% by weight of the composition and (d) the rosmarinus officinalis or origanum vulgare is preferably present in an amount of 0.01 to 0.5%, more preferably 0.05 to 0.2%, most preferably about 0.1% by weight of the composition.

Suitable cosmetic compositions include colour cosmetics such as lipsticks, foundation, lip balm, face cream, toner cleanse, aftersun, moisturiser, face masks and nail treatments. Suitable formulation types include gels, creams, serums, pastes, lotions, milks, ointments, salves, sticks, spray, roll-on, powder, solution, suspension dispersion and emulsions, be they w/o, o/w, w/o/w or o/w/o.

A particularly preferred cosmetic composition is a sunscreen.

The sunscreen may contain organic or inorganic sun filters or a combination of the two. Suitable inorganic sunfilters include:

a) Microfine titanium dioxide b) Microfine zinc oxide c) Boron nitride

Suitable organic sunscreens include:
a) p-aminobenzoic acids, their esters and derivatives (for example, 2-ethylhexyl p-dimethylaminobenzoate),
b) methoxycinnamate esters (for example, 2-ethylhexyl p-methoxycinnamate, 2-ethoxyethyl p-methoxycinnamate or α,β-di-(p-methoxycinnamoyl-α'-(2-ethylhexanoyl)glycerin,
c) benzophenones (for example oxybenzone),
d) dibenzoylmethanes such as 4-(tert-butyl)-4'-methoxydibenzoylmethane,
e) 2-phenylbenzimidazole-5 sulfonic acid and its salts,
f) alkyl-β,β-diphenylacrylates for example alkyl α-cyano-β,β-diphenylacrylates such as octocrylene,
g) triazines such as 2,4,6-trianilino-(p-carbo-2-ethyl-hexyl-1-oxi)-1,3,5 triazine,
h) camphor derivatives such as methylbenzylidene camphor Any sunscreening agent is present in an amount from 0.1 to 10% by weight of the composition.

Sunscreen composition may be formulated as any suitable form, as known to a man skilled in the art. Particularly preferred formulation types are emulsions and oily dispersions.

A skin care composition containing a synergistic combination of antioxidant agents has a multitude of advantages. Such antioxidant agents are usually highly coloured. If they are used in amounts necessary to be totally effective, it is likely that the agents would give the composition a cosmetically unacceptable appearance. Thus most conventional skin care compositions use less of an antioxidant agent than necessary to provide total protection. With the present invention because of the increased efficacy of the synergistic mixture of antioxidant agents it is possible to include the antioxidant agents in sufficient amounts to provide an effective defence against the action of free radicals. Thus use of the composition will give the users' skin improved protection from damage. All this is provided without the aforementioned disadvantage of unacceptable cosmetic appearance.

Alternatively, if the same level of protection as a conventional formulation is required, then the increased efficacy of the synergistic mixture of antioxidant agents means that the composition will require much lower quantities of the antioxidant agents than a conventional formulation. Not only are any problems with highly coloured formulations reduced (cosmetic appearance), but the cost of the formulation is likely to be cheaper as well.

Further components may be added to the skin care composition as is well-known to those skilled in the art.

Suitable oils for the oil phase of the oily dispersions and the oil phase of the water-in-oil and oil-in-water emulsions of the present invention may comprise for example:
a) hydrocarbon oils such as paraffin or mineral oils;
b) waxes such as beeswax or paraffin wax;
c) natural oils such as sunflower oil, apricot kernel oil, shea butter or jojoba oil;
d) silicone oils such as dimethicone, cyclomethicone or cetyldimethicone;
e) fatty acid esters such as isopropyl palmitate or isopropyl myristate;
f) fatty alcohols such as cetyl alcohol or stearyl alcohol; or
g) mixtures thereof, for example, the blend of waxes available commercially under the trade name Cutina (Henkel).

The emulsifiers used may be any emulsifiers known in the art for use in water-in-oil or oil-in-water emulsions. It has been found that particularly effective water-in-oil and oil-in-water sunscreen compositions can be prepared by using an emulsifier or mixture of emulsifiers selected from known cosmetically acceptable emulsifiers which include:
a) sesquioleates such as sorbitan sesquioleate, available commercially for example under the trade name Ariacel 83 (ICI), or polyglyceryl-2-sesquioleate;
b) ethoxylated esters of derivatives of natural oils such as the polyethoxylated ester of hydrogenated castor oil available commercially for example under the trade name Ariacel 989 (ICI);
c) silicone emulsifiers such as silicone polyols available commercially for example under the trade name ABIL WS08 (Th. Goldschmidt AG);
d) anionic emulsifiers such as fatty acid soaps e.g. potassium stearate and fatty acid sulphates e.g. sodium cetostearyl sulphate available commercially under the trade name Dehydag (Henkel);
e) ethoxylated fatty alcohols, for example the emulsifiers available commercially under the trade name Brij (ICI);
f) sorbitan esters, for example the emulsifiers available commercially under the trade name Span (ICI);
g) ethoxylated sorbitan esters, for example the emulsifiers available commercially under the trade name Tween (ICI);
h) ethoxylated fatty acid esters such as ethoxylated stearates, for example the emulsifiers available commercially under the trade name Myri (ICI);
i) ethoxylated mono-, di-, and tri-glycerides, for example the emulsifiers available commercially under the trade name Labrafil (Alfa Chem.);
j) non-ionic self-emulsifying waxes, for example the wax available commercially under the trade name Polawax (Croda);
k) ethoxylated fatty acids, for example, the emulsifiers available commercially under the trade name Tefose (Alfa Chem.); or
l) mixtures thereof.

For example, preservatives may be added to the composition such as 2-bromo-2-nitropropane-1,3-diol (bronopol, which is available commercially under the trade name Myacide ™), benzyl alcohol, diazolidinyl urea, imidazolidinyl urea, methyl paraben, phenoxy ethanol, propyl paraben, sodium methyl paraben, sodium dehydroacetate, polyhexamethylenebiguanide hydrochloride, isothiazolone and sodium propyl paraben, suitably in an amount of from about 0.01% to about 10% by weight of the composition.

Thickeners, viscosity modifying agents and/or gelling agents may be added to the composition, such as acrylic acid polymers e.g. available commercially under the trade name Carbopol (B.F. Goodrich) or modified celluloses e.g. hydroxyethylcellulose available commercially under the trade name Natrosol (Hercules) or hydroxypropylmethyl cellulose, amine oxides, block polymers of ethylene oxide and propylene oxide (for example, those available from BASF Wyandotte under the trade name "Pluronic" ™), PVM, MA, or a decadiene crosspolymer (available under the trade name Stabilez 60), ethoxylated fatty alcohols, salt (NaCl), phthalic acid amide, polyvinyl alcohols, fatty alcohols and alkyl galactmanans available under the trade name N-Hance from Hercules, suitably in an amount of from about 0.5% to about 10% by weight of the composition.

Sequestering agents may be added to the composition, such as ethylenediamine tetraacetic acid and salts thereof, suitably in an amount of from about 0.005% to about 0.5% by weight of the composition.

The composition may also include vitamins such as biotin, suitably in an amount of from about 0.01% to about 1.0% by weight of the composition.

The composition may also include waxes such as cocoa butter suitably in an amount of from about 1% to about 99% by weight of the composition.

The composition may also comprise suitable, cosmetically acceptable diluents, carriers and/or propellants such as dimethyl ether.

The composition may also include pearlising agents such as stearic monoethanolamide, suitably in an amount of from about 0.01% to about 10% by weight of the composition.

Perfumes may be added suitably in an amount of from about 0.01% to about 2% by weight of the composition, as may water soluble dyes such as tartrazine, suitably in an amount of from about a trace amount (such as $1\times10^{-5}$%) to about 0.1% by weight of the composition.

The composition may also include pH adjusting agents such as sodium hydroxide, aminomethyl propanol, triethanolamine, suitably in an amount of from about 0.01% to about 10% by weight of the composition.

The composition may be buffered by means well known in the art, for example by use of buffer systems comprising succinic acid, citric acid, lactic acid, and acceptable salts thereof, phosphoric acid, mono- or disodium phosphate and sodium carbonate. Suitably, the composition may have a pH between about 3 and about 10, preferably between about 4 and about 8.

The compositions of the present invention may additionally comprise other components which will be well known to those skilled in the art. These include, for example, emolients such as isopropyl myristate or triglycerides of fatty acids e.g. lauric triglyceride or capric/caprylic triglyceride, such as the triglyceride available commercially under the trade name Migliol 810 (Huls UK); moisturisers such as D-panthenol; humectants such as glycerin or 1,3-butylene glycol; antioxidants such as DL-α-tocopherylacetate or butylated hydroxytoluene; emulsion stabilising salts such as sodium chloride, sodium citrate or magnesium sulphate; film formers to assist spreading on the surface of the skin such as alkylated polyvinylpyrrolidone e.g. available commercially under the trade name Antaron (GAF) and colourings.

Broadly in accordance with a further aspect of the present invention there is provided a method of preparing a skin care composition. Optionally any other suitable ingredients may be added such as those described herein. Preferred methods of preparation are described in the examples.

The invention will be understood with reference to the non-limiting tests and formulation examples described hereinafter:

EXAMPLE 1

Aftersun Treatment Lotion

|  | % w/w |
|---|---|
| Aqua | to 100 |
| Hydrated silica | 5 |
| Isopropyl palmitate | 4 |
| Arachidyl propionate | 2 |
| Dimethicone | 2 |
| Glycerin | 2 |
| Steareth-21 | 1.96 |
| Steareth-2 | 1.683 |
| Cetyl alcohol | 1 |
| Tribehenin | 1 |
| Glyceryl stearate | 1 |
| Paraffinum liquidum | 0.994 |
| Panthenol | 0.75 |
| Parfum | 0.3 |
| Xanthan gum | 0.3 |
| Sodium citrate | 0.25 |
| Tocopheryl acetate | 0.2 |
| Hydroxyethylcellulose | 0.1 |
| Bisabolol | 0.095 |
| Citric acid | 0.05 |
| Preservative | q.s |
| Sodium ascorbyl phosphate | 0.15 |
| Morus alba | 0.0023 |
| Panax ginseng | 0.03 |

Method

Stage 1

The citric acid, sodium citrate and hydroxyethylcellulose are added to the water. Using a propellor stirrer, the mixture is stirred until dispersed. The xanthan gum is pre-dispersed in the glycerin and this is then added to the bulk, which is then heated to 70° C.

Stage 2

The isopropyl palmitate, arachidyl propionate, dimethicone, steareth-21, steareth-2, cetyl alcohol, tribehenin, glyceryl stearate, paraffinum liquidum are mixed and heated to 70° C. to melt the waxes.

Stage 3

Using a homogeniser, stage 2 is added to stage 1 and is mixed until emulsified and uniform. The emulsion is cooled to below 35° C. using stirring. Once below 35° C., the remaining materials are added, including the antioxidant complex. The product is made to weight using purified water, and mixed until uniform.

EXAMPLE 2

Aftersun Treatment Lotion

|  | % w/w |
|---|---|
| Aqua | to 100 |
| Hydrated silica | 5 |
| Isopropyl palmitate | 4 |
| Arachidyl propionate | 2 |
| Dimethicone | 2 |
| Glycerin | 2 |
| Steareth-21 | 1.96 |
| Steareth-2 | 1.683 |
| Cetyl alcohol | 1 |
| Tribehenin | 1 |
| Glyceryl stearate | 1 |
| Paraffinum liquidum | 0.994 |
| Panthenol | 0.75 |
| Parfum | 0.3 |
| Xanthan gum | 0.3 |
| Sodium citrate | 0.25 |
| Tocopheryl acetate | 0.2 |
| Hydroxyethylcellulose | 0.1 |
| Bisabolol | 0.095 |
| Citric acid | 0.05 |
| Preservative | q.s |
| Magnesium ascorbyl phosphate | 0.15 |
| Morus alba | 0.0023 |
| Panax ginseng | 0.03 |

Method

Stage 1

The citric acid, sodium citrate and hydroxyethylcellulose are added to the water. Using a propellor stirrer, the mixture is stirred until dispersed. The xanthan gum is pre-dispersed in the glycerin and this is then added to the bulk, which is then heated to 70° C.

Stage 2

The isopropyl palmitate, arachidyl propionate, dimethicone, steareth-21, steareth-2, cetyl alcohol, tribehenin, glyceryl stearate, paraffinum liquidum are mixed and heated to 70° C. to melt the waxes.

Stage 3

Using a homogeniser, stage 2 is added to stage 1 and is mixed until emulsified and uniform. The emulsion is cooled to below 35° C. using stirring.

Once below 35° C., the remaining materials are added, including the antioxidant complex. The product is made to weight using purified water, and mixed until uniform.

EXAMPLE 3

Anti-Ageing Day Cream

|  | % w/w |
|---|---|
| Aqua | to 100 |
| Butylene glycol | 5 |
| Dicaprylyl maleate | 4 |
| Paraffinum liquidum | 4 |
| Octyl methoxycinnamate | 3 |
| Petrolatum | 3 |
| Cetyl Alcohol | 2 |
| Glycerin | 2 |
| Dimethicone | 2 |
| Cetearyl alcohol | 1.6 |
| Butyl methoxydibenzoylmethane | 1 |
| Hydroxyethylcellulose | 0.4 |
| PEG-20 stearate | 0.4 |
| Polyacrylamide | 0.4 |
| Parfum | 0.3 |
| C13–14 isoparaffin | 0.215 |
| Retinyl palmitate | 0.1782 |
| Tetrasodium EDTA | 0.1 |
| Citric acid | 0.08 |
| Laureth-7 | 0.055 |
| BHT | 0.0024 |
| Sodium ascorbyl phosphate | 1.5 |
| Morus alba | 0.0023 |
| Panax ginseng | 0.03 |
| Preservative | q.s |

Method

Stage 1

Tetrasodium EDTA and citric acid are added to the water using a propellor stirrer. The hydroxyethylcellulose is added and dispersed using a homogeniser. butylene glycol, glycerin and methylparaben are added and the bulk is heated to 70° C.

Stage 2

The dicaprylyl maleate, paraffinum liquidum, octyl methoxycinnamate, petrolatum, cetyl alcohol, dimethicone, cetearyl alcohol, butyl methoxydibenzoylmethane, PEG-20 stearate, C13–14 isoparaffin, laureth-7 and BHT are mixed and heated to 70° C. to melt the waxes.

Stage 3

Using a homogeniser, stage 2 is added to stage 1 and the bulk is mixed until emulsified and stable. The product is then cooled to below 35° C. using stirring. The remaining raw materials, including the antioxidant complex are added and the product is mixed using a propellor stirrer until uniform. The product is made to weight using purified water.

EXAMPLE 4

Anti-Ageing Day Cream

|  | % w/w |
|---|---|
| Aqua | to 100 |
| Butylene glycol | 5 |
| Dicaprylyl maleate | 4 |
| Paraffinum liquidum | 4 |
| Octyl methoxycinnamate | 3 |
| Petrolatum | 3 |
| Cetyl Alcohol | 2 |
| Glycerin | 2 |
| Dimethicone | 2 |
| Cetearyl alcohol | 1.6 |
| Butyl methoxydibenzoylmethane | 1 |
| Hydroxyethylcellulose | 0.4 |
| PEG-20 stearate | 0.4 |
| Polyacrylamide | 0.4 |
| Parfum | 0.3 |
| C13–14 isoparaffin | 0.215 |
| Retinyl palmitate | 0.1782 |
| Tetrasodium EDTA | 0.1 |
| Citric acid | 0.08 |

-continued

|  | % w/w |
| --- | --- |
| Laureth-7 | 0.055 |
| BHT | 0.0024 |
| Magnesium ascorbyl phosphate | 1.5 |
| Morus alba | 0.0023 |
| Panax ginseng | 0.03 |
| Preservative | q.s |

Method

Stage 1

Tetrasodium EDTA and citric acid are added to the water using a propellor stirrer. The hydroxyethylcellulose is added and dispersed using a homogeniser butylene glycol, glycerin and methylparaben are added and the bulk is heated to 70° C.

Stage 2

The dicaprylyl maleate, paraffinum liquidum, octyl methoxycinnamate, petrolatum, cetyl alcohol, dimethicone, cetearyl alcohol, butyl methoxydibenzoylmethane, PEG-20 stearate, C13-14 isoparaffin, laureth-7 and BHT are mixed and heated to 70° C. to melt the waxes.

Stage 3

Using a homogeniser, stage 2 is added to stage 1 and the bulk is mixed until emulsified and stable. The product is then cooled to below 35° C. using stirring. The remaining raw materials, including the antioxidant complex are added and the product is mixed using a propellor stirrer until uniform. The product is made to weight using purified water.

EXAMPLE 5

Sun Protection Lotion SPF8

|  | % w/w |
| --- | --- |
| Aqua | to 100 |
| C12–15 Alkyl Benzoate | 8 |
| Butylene glycol | 5 |
| Butyl methoxydibenzoylmethane | 2.2 |
| Dimethicone | 2 |
| Polyglyceryl-3 methylglucose distearate | 2 |
| PVP/hexadecene copolymer | 1.75 |
| Octyl methoxycinnamate | 1.7 |
| Theobroma cacao | 0.5 |
| Parfum | 0.5 |
| Tocopheryl acetate | 0.2 |
| Acrylates/vinyl isodecanoate crosspolymer | 0.15 |
| Potassium hydroxide | 0.034 |
| Tetrasodium EDTA | 0.02 |
| Preservative | q.s |
| Sodium ascorbyl phosphate | 0.15 |
| Morus alba | 0.0023 |
| Panax ginseng | 0.03 |

Method

Stage 1

The EDTA is dispersed into the water. Using a propellor stirrer, the acrylates/vinyl isodecanoate crosspolymer are added and dispersed and hydrated. Butylene glycol is added and the aqueous phase is heated to 70° C.

Stage 2

The C12-15 alkyl benzoate, butyl methoxydibenzoylmethane, dimethicone, polyglyceryl-3 methylglucose distearate, PVP/hexadecene copolymer, octyl methoxycinnamate, theobroma cacao and tocopheryl acetate are mixed and heated to 70° C. to melt the waxes.

Stage 3

Using a homogeniser, stage 2 is added to stage 1 and the bulk is mixed until emulsified and uniform. The emulsion is cooled to below 35° C. with stirring. The remaining materials, including the antioxidant complex are added and mixed. The product is made to weight using purified water and stirred until uniform.

EXAMPLE 6

Sun Protection Lotion SPF8

|  | % w/w |
| --- | --- |
| Aqua | to 100 |
| C12–15 Alkyl Benzoate | 8 |
| Butylene glycol | 5 |
| Butyl methoxydibenzoylmethane | 2.2 |
| Dimethicone | 2 |
| Polyglyceryl-3 methylglucose distearate | 2 |
| PVP/hexadecene copolymer | 1.75 |
| Octyl methoxycinnamate | 1.7 |
| Theobroma cacao | 0.5 |
| Parfum | 0.5 |
| Tocopheryl acetate | 0.2 |
| Acrylates/vinyl isodecanoate crosspolymer | 0.15 |
| Potassium hydroxide | 0.034 |
| Tetrasodium EDTA | 0.02 |
| Preservative | q.s |
| Magnesium ascorbyl phosphate | 0.15 |
| Morus alba | 0.0023 |
| Panax ginseng | 0.03 |

Method

Stage 1

The EDTA is dispersed into the water. Using a propellor stirrer, the acrylates/vinyl isodecanoate crosspolymer are added and dispersed and hydrated. Butylene glycol is added and the aqueous phase is heated to 70° C.

Stage 2

The C12-15 alkyl benzoate, butyl methoxydibenzoylmethane, dimethicone, polyglyceryl-3 methylglucose distearate, PVP/hexadecene copolymer, octyl methoxycinnamate, theobroma cacao and tocopheryl acetate are mixed and heated to 70° C. to melt the waxes.

Stage 3

Using a homogeniser, stage 2 is added to stage 1 and the bulk is mixed until emulsified and uniform. The emulsion is cooled to below 35° C. with stirring. The remaining materials, including the antioxidant complex are added and mixed. The product is made to weight using purified water and stirred until uniform.

EXAMPLE 7

Aftersun Treatment

|  | % w/w |
|---|---|
| Aqua | to 100 |
| Petrolatum | 3 |
| Cetyl Alcohol | 2 |
| Dimethicone | 2 |
| Glycerin | 2 |
| Ceteath-20 | 1.7 |
| Paraffinum Liquidum | 1 |
| Sodium chloride | 0.8 |
| Theobroma cacao | 0.7 |
| Glyceryl stearate | 0.5 |
| Parfum | 0.3 |
| Allantoin | 0.2 |
| Hydroxyethylcellulose | 0.1 |
| Triclosan | 0.1 |
| Citric acid | 0.02 |
| Preservative | q.s |
| Sodium ascorbyl phosphate | 0.15 |
| Morus alba | 0.0023 |
| Panax ginseng | 0.03 |

Method

Stage 1

Into the water, sodium chloride and citric acid are added and dispersed. Using a propellor stirrer, hydroxyethylcellulose is added and dispersed. This phase is then heated to 70° C.

Stage 2

The petrolatum, cetyl alcohol, dimethicone, ceteath-20, paraffinum liquidum, theobroma cacao and glyceryl stearate are mixed and heated to 70° C. to melt the waxes.

Stage 3

Using a homogeniser, stage 2 is added to stage 1, this is mixed until emulsified and uniform. The emulsion is then cooled to below 35° C. with stirring. The remaining materials, including the antioxidant complex are then added and mixed. The product is made to weight using purified water and stirred until uniform.

EXAMPLE 8

Aftersun Treatment

|  | % w/w |
|---|---|
| Aqua | to 100 |
| Petrolatum | 3 |
| Cetyl Alcohol | 2 |
| Dimethicone | 2 |
| Glycerin | 2 |
| Ceteath-20 | 1.7 |
| Paraffinum Liquidum | 1 |
| Sodium chloride | 0.8 |
| Theobroma cacao | 0.7 |
| Glyceryl stearate | 0.5 |
| Parfum | 0.3 |
| Allantoin | 0.2 |
| Hydroxyethylcellulose | 0.1 |
| Triclosan | 0.1 |
| Citric acid | 0.02 |
| Preservative | q.s |
| Magnesium ascorbyl phosphate | 0.15 |
| Morus alba | 0.0023 |
| Panax ginseng | 0.03 |

Method

Stage 1

Into the water, sodium chloride and citric acid are added and dispersed. Using a propellor stirrer, hydroxyethylcellulose is added and dispersed. This phase is then heated to 70° C.

Stage 2

The petrolatum, cetyl alcohol, dimethicone, ceteath-20, paraffinum liquidum, theobroma cacao and glyceryl stearate are mixed and heated to 70° C. to melt the waxes.

Stage 3

Using a homogeniser, stage 2 is added to stage 1, this is mixed until emulsified and uniform. The emulsion is then cooled to below 35° C. with stirring. The remaining materials, including the antioxidant complex are then added and mixed. The product is made to weight using purified water and stirred until uniform.

EXAMPLE 9

Eve Contour Treatment Cream

|  | % w/w |
|---|---|
| Aqua | to 100 |
| Butylene glycol | 6 |
| Paraffinum liquidum | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| Prunus dulcis | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| Sodium ascorbyl phosphate | 1.5 |
| Morus alba | 0.023 |
| Panax ginseng | 0.03 |
| Preservative | q.s |

Method

Stage 1

Into the water, citric acid, EDTA, sodium phosphate, disodium phosphate and lactic acid are added and dispersed. Using a homogeniser, carbomer is added and hydrated. The aqueous phase is then heated to 70° C.

Stage 2

The paraffinum liquidum, octyl methoxycinnamate, dimethicone, petrolatum, cetearyl octanoate, cetearyl alcohol, glyceryl stearate, cetyl alcohol, hydrogenated vegetable glycerides citrate, tocopheryl acetate, PEG-20 stearate, isopropyl myristate and PEG-12 isostearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 10

Eve Contour Treatment Cream

|  | % w/w |
| --- | --- |
| Aqua | to 100 |
| Butylene glycol | 6 |
| Paraffinum liquidum | 5 |
| Octyl methoxycinnamate | 4 |
| Dimethicone | 2 |
| Petrolutum | 2 |
| Cetearyl octanoate | 1.8 |
| Cetearyl alcohol | 1.6 |
| Glyceryl stearate | 1.5 |
| Cetyl alcohol | 1 |
| Prunus dulcis | 1 |
| Glycerin | 0.57 |
| Hydrogenated vegetable glycerides citrate | 0.5 |
| Tocopheryl acetate | 0.5 |
| Bisabolol | 0.475 |
| Panthenol | 0.45 |
| Sodium phosphate | 0.42 |
| PEG-20 stearate | 0.4 |
| Isopropyl myristate | 0.2 |
| Carbomer | 0.15 |
| PEG-12 isostearate | 0.125 |
| Allantoin | 0.1 |
| Tetrasodium EDTA | 0.1 |
| Lactic acid | 0.088 |
| Disodium phophate | 0.083 |
| Potassium hydroxide | 0.051 |
| Magnesium ascorbyl phosphate | 1.5 |
| Morus alba | 0.023 |
| Panax ginseng | 0.03 |
| Preservative | q.s |

Method

Stage 1

Into the water, citric acid, EDTA, sodium phosphate, disodium phosphate and lactic acid are added and dispersed. Using a homogeniser, carbomer is added and hydrated. The aqueous phase is then heated to 70° C.

Stage 2

The paraffinum liquidum, octyl methoxycinnamate, dimethicone, petrolatum, cetearyl octanoate, cetearyl alcohol, glyceryl stearate, cetyl alcohol, hydrogenated vegetable glycerides citrate, tocopheryl acetate, PEG-20 stearate, isopropyl myristate and PEG-12 isostearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 11

Skin Refreshing Cream

|  | % w/w |
| --- | --- |
| Aqua | to 100 |
| Butylene glycol | 7.5 |
| Silica | 7.2 |
| Arabinogalactan | 5.35 |
| Dimethicone | 5.35 |
| Petrolatum | 5.35 |
| Hydrated silica | 3.75 |
| Steareth-2 | 2.7 |
| Prunus dulcis | 2.7 |
| Steareth-21 | 0.9 |
| PVP/hexadecene copolymer | 0.8 |
| Carbomer | 0.32 |
| Sodium PCA | 0.2 |
| Parfum | 0.2 |
| Hydroxyethylcellulose | 0.16 |
| Potassium hydroxide | 0.1 |
| Propylene glycol | 0.1 |
| Magnesium ascorbyl phosphate | 1.5 |
| Morus alba | 0.0023 |
| Panax ginseng | 0.03 |
| Preservative | q.s |

Method

Stage 1

Into the water, the carbomer is added and hydrated using a homogeniser. The aqueous phase is then heated to 70° C.

Stage 2

The silica, arabinogalactan, PVP/hexadecene copolymer, dimethicone, petrolatum, hydrated silica, steareth-2 and steareth-21 are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 12

Daily Skin Protection Lotion

|  | % w/w |
|---|---|
| Aqua | to 100 |
| Dimethicone | 5 |
| Glycerin | 3 |
| Kaolin | 3 |
| Dicaprylyl maleate | 2.5 |
| Isopropyl myristate | 2.5 |
| Stearate-2 | 2 |
| Octyl methoxycinnamate | 1 |
| Steareth-21 | 1 |
| Cetyl alcohol | 0.75 |
| Butyl methoxydibenzoylmethane | 0.5 |
| Propylene glycol | 0.5 |
| Hydroxyethylcellulose | 0.4 |
| Xanthan gum | 0.24 |
| Serica | 0.1 |
| Sodium C8–16 isoalkylsuccinyl lactoglobulin sulfonate | 0.1 |
| Tetrasodium EDTA | 0.1 |
| Citric acid | 0.05 |
| Magnesium ascorbyl phosphate | 1.5 |
| Morus alba | 0.0023 |
| Panax ginseng | 0.03 |
| Preservative | q.s |

Method

Stage 1

Into the water, the citric acid and EDTA are added and dispersed. The hydroxyethylcellulose is added and hydrated using a propellor stirrer. Xanthan gum is pre-dispersed in glycerin and added to the bulk. This is stirred until uniform. The aqueous phase is then heated to 70° C.

Stage 2

The dimethicone, dicaprylyl maleate, isopropyl myristate, stearate-2, octyl methoxycinnamate, steareth-21, cetyl alcohol and butyl methoxydibenzoylmethane are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 13

Anti-Ageing Night Cream

|  | % w/w |
|---|---|
| Aqua | to 100 |
| Glycerin | 5 |
| Paraffinum liquidum | 4.5 |
| Dicaprylyl maleate | 3 |
| Dimethicone | 3 |
| Petrolatum | 3 |
| Paraffin | 2.9 |
| Cetyl alcohol | 2 |
| Steareth-2 | 2 |
| Glyceryl stearate | 1.5 |
| Butyrospermum parkii | 1.5 |
| Steareth-21 | 1 |
| Mannitol | 1 |
| Cera microcristallina | 0.262 |
| Buxus chinensis | 0.5 |
| Propylene glycol | 0.48 |
| Parfum | 0.4 |
| Borago officinalis | 0.3 |
| Hydroxyethylcellulose | 0.3 |
| Lactis proteinum | 0.3 |
| Xanthan gum | 0.25 |
| Alcohol denat. | 0.08 |
| Sodium citrate | 0.08 |
| Lecithin | 0.075 |
| BHT | 0.05 |
| Faex | 0.04 |
| Phospholipids | 0.03 |
| Citric acid | 0.025 |
| Magnesium ascorbyl phosphate | 1.5 |
| Morus alba | 0.0023 |
| Panax ginseng | 0.03 |
| Preservative | q.s |

Method

Stage 1

Into the water, the citric add and sodium citrate are added and dispersed. The hydroxyethylcellulose is added and hydrated using a propellor stirrer. Xanthan gum is pre-dispersed in glycerin and added to the bulk. This is stirred until uniform. The aqueous phase is then heated to 70° C.

Stage 2

The paraffinum liquidum, dicaprylyl maleate, dimethicone, petrolatum, paraffin, cetyl alcohol, steareth-2, glyceryl stearate, steareth-21, cera microcristallina and BHT are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 14

Sun Protection Lotion for Sensitive Skin—SPF15

|  | % w/w |
|---|---|
| Aqua | to 100 |
| C12–15 alkyl benzoate | 12 |
| Butylene glycol | 5 |
| Octyl methoxycinnamate | 3.8 |
| Butyl methoxydibenzoylmethane | 3 |
| Dimethicone | 2 |
| Polyglyceryl-3 methylglucose distearate | 2 |
| PVP/hexadecene copolymer | 1.75 |
| C18–36 acid glycol ester | 1.5 |
| Polysorbate 60 | 0.5 |
| Titanium dioxide | 0.3 |
| Tocopheryl acetate | 0.2 |
| Acrylates/vinyl isodecanoate crosspolymer | 0.14 |
| Potassium hydroxide | 0.035 |
| Tetrasodium EDTA | 0.02 |

-continued

|  | % w/w |
| --- | --- |
| Preservative | q.s |
| Sodium ascorbyl phosphate | 0.15 |
| Morus alba | 0.0023 |
| Panax ginseng | 0.03 |

Method

Stage 1

Into the water, citric acid is added and dispersed. The acrlyates/vinyl isodecanoate crosspolymer are added and dispersed using a propellor stirrer. The aqueous phase is then heated to 70° C.

Stage 2

The C12-15 alkyl benzoate, PVP/hexadecene copolymer, octyl methoxycinnamate, butyl methoxydibenzoylmethane, dimethicone, polyglyceryl-3 methylglucose distearate, C18-36 acid glycol ester, polysorbate 60, titanium dioxide and tocopheryl acetate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 15

Sun Protection Lotion for Sensitive Skin—SPF15

|  | % w/w |
| --- | --- |
| Aqua | to 100 |
| C12–15 alkyl benzoate | 12 |
| Butylene glycol | 5 |
| Octyl methoxycinnamate | 3.8 |
| Butyl methoxydibenzoylmethane | 3 |
| Dimethicone | 2 |
| Polyglyceryl-3 methylglucose distearate | 2 |
| PVP/hexadecene copolymer | 1.75 |
| C18–36 acid glycol ester | 1.5 |
| Polysorbate 60 | 0.5 |
| Titanium dioxide | 0.3 |
| Tocopheryl acetate | 0.2 |
| Acrylates/vinyl isodecanoate crosspolymer | 0.14 |
| Potassium hydroxide | 0.035 |
| Tetrasodium EDTA | 0.02 |
| Preservative | q.s |
| Magnesium ascorbyl phosphate | 0.15 |
| Morus alba | 0.0023 |
| Panax ginseng | 0.03 |

Method

Stage 1

Into the water, citric acid is added and dispersed. The acrlyates/vinyl isodecanoate crosspolymer are added and dispersed using a propellor stirrer. The aqueous phase is then heated to 70° C.

Stage 2

The C12-15 alkyl benzoate, PVP/hexadecene copolymer, octyl methoxycinnamate, butyl methoxydibenzoylmethane, dimethicone, polyglyceryl-3 methylglucose distearate, C18-36 acid glycol ester, polysorbate 60, titanium dioxide and tocopheryl acetate are heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 16

Sun Protection Cream for Sensitive Skin

|  | % w/w |
| --- | --- |
| Aqua | to 100 |
| Octyl stearate | 13.5 |
| Zinc oxide | 13.5 |
| Isopropyl myristate | 5 |
| Butylene glycol | 3 |
| Isohexadecane | 3 |
| Titanium dioxide | 2 |
| Polyglyceryl-3 oleate | 1.75 |
| Cetyl dimethicone copolyol | 1.35 |
| Magnesium sulfate | 0.75 |
| Sodium chloride | 0.75 |
| Aluminium stearate | 0.18 |
| Alumina | 0.15 |
| Lecithin | 0.13 |
| Isopropyl palmitate | 0.05 |
| Sodium ascorbyl phosphate | 0.15 |
| Morus alba | 0.0023 |
| Panax ginseng | 0.03 |

Method

Stage 1

Into the water, magnesium sulfate, sodium chloride and butylene glycol are added and dispersed. The aqueous phase is then heated to 70° C.

Stage 2

The octyl stearate, isopropyl myristate, isohexadecane, titanium dioxide, polyglyceryl-3 oleate, cetyl dimethicone copolyol, aluminium stearate, lecithin and isopropyl palmitate are mixed and heated to 70° C. to melt the waxes.

Stage 3

Using a propellor stirrer, stage 2 is added to stage 1. Once uniform, the emulsion is transferred to a homogeniser and mixed to generate the viscosity. The emulsion is then cooled to below 35° C. using stirring. The remaining materials, including the antioxidant complex are then added and mixed. The product is then made to weight using purified water and is stirred until uniform.

EXAMPLE 17

Sun Protection Cream for Sensitive Skin

|  | % w/w |
|---|---|
| Aqua | to 100 |
| Octyl stearate | 13.5 |
| Zinc oxide | 13.5 |
| Isopropyl myristate | 5 |
| Butylene glycol | 3 |
| Isohexadecane | 3 |
| Titanium dioxide | 2 |
| Polyglyceryl-3 oleate | 1.75 |
| Cetyl dimethicone copolyol | 1.35 |
| Magnesium sulfate | 0.75 |
| Sodium chloride | 0.75 |
| Aluminium stearate | 0.18 |
| Alumina | 0.15 |
| Lecithin | 0.13 |
| Isopropyl palmitate | 0.05 |
| Magnesium ascorbyl phosphate | 0.15 |
| *Morus alba* | 0.0023 |
| Panax ginseng | 0.03 |

Method

Stage 1

Into the water, magnesium sulfate, sodium chloride and butylene glycol are added and dispersed. The aqueous phase is then heated to 70° C.

Stage 2

The octyl stearate, isopropyl myristate, isohexadecane, titanium dioxide, polyglyceryl-3 oleate, cetyl dimethicone copolyol, aluminium stearate, lecithin and isopropyl palmitate are mixed and heated to 70° C. to melt the waxes.

Stage 3

Using a propellor stirrer, stage 2 is added to stage 1. Once uniform, the emulsion is transferred to a homogeniser and mixed to generate the viscosity. The emulsion is then cooled to below 35° C. using stirring. The remaining materials, including the antioxidant complex are then added and mixed. The product is then made to weight using purified water and is stirred until uniform.

EXAMPLE 18

Anti-Ageing Foundation

|  | % w/w |
|---|---|
| Aqua | to 100 |
| Butylene glycol | 9.8 |
| Cetearyl isononanoate | 4.9 |
| Dimethicone | 3.2 |
| Glycerin | 1.96 |
| Silica | 1.9 |
| Caprylic/capric triglyceride | 1.67 |
| Paraffinum liquidum | 1.67 |
| Petrolatum | 1.67 |
| Hydrogenated coco-glycerides | 1.67 |
| Cetearyl octanoate | 1.5 |
| Cetearyl alcohol | 1.35 |
| Octyl methoxycinnamate | 1.28 |
| Talc | 1 |
| Glyceryl stearate | 0.95 |

-continued

|  | % w/w |
|---|---|
| PEG-100 stearate | 0.9 |
| Butyl methoxydibenzoylmethane | 0.6 |
| Saccharide isomerate | 0.54 |
| Lactic acid | 0.45 |
| Sodium polyacrylate | 0.45 |
| Boron nitride | 0.42 |
| Sodium PCA | 0.4 |
| *Borago officinalis* | 0.4 |
| Tocopheryl acetate | 0.4 |
| PVP/hexadecene copolymer | 0.4 |
| PEG-20 stearate | 0.33 |
| Glycolic acid | 0.2 |
| Sodium stearoyl lactylate | 0.2 |
| Isopropyl myristate | 0.17 |
| Polyaminopropyl biguanide | 0.16 |
| Tetrasodium EDTA | 0.1 |
| Xanthan gum | 0.1 |
| Citric acid | 0.06 |
| Alcohol denat. | 0.04 |
| Lecithin | 0.037 |
| Preservative | q.s |
| *Rosmarinus officinalis* | 0.1 |
| *Morus alba* | 0.0023 |
| Panax ginseng | 0.03 |

Method

Stage 1

Into the water, citric acid, EDTA and lactic acid are added and dispersed. Xanthan gum is pre-dispersed in butylene glycol and is added to the bulk. The aqueous phase is then heated to 70° C.

Stage 2

The cetearyl isononanoate, dimethicone, silica, PVP/hexadecene copolymer, caprylic/capric triglyceride, paraffinum liquidum, petrolatum, hydrogenated coco-glycerides, cetearyl octanoate, cetearyl alcohol, octyl methoxycinnamate, talc, glyceryl stearate, PEG-100 stearate, butyl methoxydibenzoylmethane, borago officinalis, tocopheryl acetate, sodium stearoyl lactylate, isopropyl myristate and lecithinoil phase are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 19

Anti-Ageing Foundation

|  | % w/w |
|---|---|
| Aqua | to 100 |
| Butylene glycol | 9.8 |
| Cetearyl isononanoate | 4.9 |
| Dimethicone | 3.2 |
| Glycerin | 1.96 |
| Silica | 1.9 |
| Caprylic/capric triglyceride | 1.67 |
| Paraffinum liquidum | 1.67 |

-continued

|  | % w/w |
| --- | --- |
| Petrolatum | 1.67 |
| Hydrogenated coco-glycerides | 1.67 |
| Cetearyl octanoate | 1.5 |
| Cetearyl alcohol | 1.35 |
| Octyl methoxycinnamate | 1.28 |
| Talc | 1 |
| Glyceryl stearate | 0.95 |
| PEG-100 stearate | 0.9 |
| Butyl methoxydibenzoylmethane | 0.6 |
| Saccharide isomerate | 0.54 |
| Lactic acid | 0.45 |
| Sodium polyacrylate | 0.45 |
| Boron nitride | 0.42 |
| Sodium PCA | 0.4 |
| *Borago officinalis* | 0.4 |
| Tocopheryl acetate | 0.4 |
| PVP/hexadecene copolymer | 0.4 |
| PEG-20 stearate | 0.33 |
| Glycolic acid | 0.2 |
| Sodium stearoyl lactylate | 0.2 |
| Isopropyl myristate | 0.17 |
| Polyaminopropyl biguanide | 0.16 |
| Tetrasodium EDTA | 0.1 |
| Xanthan gum | 0.1 |
| Citric acid | 0.06 |
| Alcohol denat. | 0.04 |
| Lecithin | 0.037 |
| Preservative | q.s |
| *Origanum vulgare* | 0.1 |
| *Morus alba* | 0.0023 |
| *Panax ginseng* | 0.03 |

Method

Stage 1

Into the water, citric acid, EDTA and Lactic acid are added and dispersed. Xanthan gum is pre-dispersed in butylene glycol and is added to the bulk. The aqueous phase is then heated to 70° C.

Stage 2

The cetearyl isononanoate, dimethicone, Silica, PVP/hexadecene copolymer, caprylic/capric triglyceride, paraffinum liquidum, petrolatum, hydrogenated coco-glycerides, cetearyl octanoate, cetearyl alcohol, octyl methoxycinnamate, talc, glyceryl stearate, PEG-100 stearate, butyl methoxydibenzoylmethane, borago officinalis, tocopheryl acetate, sodium stearoyl lactylate, isopropyl myristate and lecithinoil phase are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 20

Sun Protection Spray—SPF15

|  | % w/w |  |
| --- | --- | --- |
| Aqua | to | 100 |
| Dicaprylyl maleate | 12 |  |
| Butylene glycol | 5 |  |
| Octyl methoxycinnamate | 4 |  |
| Butyl methoxydibenzoylmethane | 3.5 |  |
| Dimethicone | 3 |  |
| Polyglyceryl-3 methylglucose distearate | 3 |  |
| Acrylates/octylacrylamide copolymer | 2 |  |
| C18–36 acid glycol ester | 1.5 |  |
| Triethanolamine | 0.5 |  |
| Tocopheryl acetate | 0.2 |  |
| Acrylates/vinyl isodecanoate crosspolymer | 0.05 |  |
| Tetrasodium EDTA | 0.02 |  |
| Potassium hydroxide | 0.015 |  |
| Preservative | q.s |  |
| Sodium ascorbyl phosphate | 0.15 |  |
| *Morus alba* | 0.0023 |  |
| *Panax ginseng* | 0.03 |  |

Method

Stage 1

Into the water, EDTA is added and dispersed. Acrylates/vinyl isodecanoate crosspolymer are added and dispersed using a propellor stirrer. Butylene glycol is added and dispersed. The aqueous phase is then heated to 70° C.

Stage 2

The dicaprylyl maleate, Acrylates/octylacrylamide copolymer, octyl methoxycinnamate, butyl methoxydibenzoylmethane, dimethicone, polyglyceryl-3 methylglucose, C18–36 acid glycol ester and tocopheryl acetate are mixed and heated to 80° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 21

Sun Protection Spray—SPF15

|  | % w/w |  |
| --- | --- | --- |
| Aqua | to | 100 |
| Dicaprylyl maleate | 12 |  |
| Butylene glycol | 5 |  |
| Octyl methoxycinnamate | 4 |  |
| Butyl methoxydibenzoylmethane | 3.5 |  |
| Dimethicone | 3 |  |
| Polyglyceryl-3 methylglucose distearate | 3 |  |
| Acrylates/octylacrylamide copolymer | 2 |  |
| C18–36 acid glycol ester | 1.5 |  |
| Triethanolamine | 0.5 |  |
| Tocopheryl acetate | 0.2 |  |
| Acrylates/vinyl isodecanoate crosspolymer | 0.05 |  |
| Tetrasodium EDTA | 0.02 |  |
| Potassium hydroxide | 0.015 |  |
| Preservative | q.s |  |
| Magnesium ascorbyl phosphate | 0.15 |  |
| *Morus alba* | 0.0023 |  |
| *Panax ginseng* | 0.03 |  |

Method

Stage 1

Into the water, EDTA is added and dispersed. Acrylates/vinyl isodecanoate crosspolymer are added and dispersed using a propellor stirrer. Butylene glycol is added and dispersed. The aqueous phase is then heated to 70° C.

Stage 2

The dicaprylyl maleate, Acrylates/octylacrylamide copolymer, octyl methoxycinnamate, butyl methoxydibenzoylmethane, dimethicone, polyglyceryl-3 methylglucose, C18–36 acid glycol ester and tocopheryl acetate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 22

Toner & Cleanser 2 in 1

|  | % w/w |
| --- | --- |
| Alcohol denat. | 48 |
| Aqua | to 100 |
| PEG-8 | 6 |
| Glycerin | 2 |
| Propylene glycol | 0.5 |
| Sodium C8–16 isoalkylsuccinyl lactoglobulin sulfonate | 0.02 |
| *Laminaria saccharina* | 0.01 |
| *Hamamelis virginiana* | 0.006 |
| *Citrullus vulgaris* | 0.001 |
| Preservative | q.s |
| Sodium ascorbyl phosphate | 1.5 |
| *Morus alba* | 0.0023 |
| *Panax ginseng* | 0.03 |

Method

Stage 1

Into the water, alcohol denat. Is added and dispersed until uniform. Using a propellor stirrer, all materials including the antioxidant complex, are slowly added and stirred until uniform. The product is made to weight using purified water and stirred until uniform.

EXAMPLE 23

Toner & Cleanser 2 in 1

|  | % w/w |
| --- | --- |
| Alcohol denat. | 48 |
| Aqua | to 100 |
| PEG-8 | 6 |
| Glycerin | 2 |
| Propylene glycol | 0.5 |
| Sodium C8–16 isoalkylsuccinyl lactoglobulin sulfonate | 0.02 |
| *Laminaria saccharina* | 0.01 |
| *Hamamelis virginiana* | 0.006 |
| *Citrullus vulgaris* | 0.001 |
| Preservative | q.s |
| Magnesium ascorbyl phosphate | 1.5 |
| *Morus alba* | 0.0023 |
| *Panax ginseng* | 0.03 |

Method.

Stage 1

Into the water, alcohol denat. Is added and dispersed until uniform. Using a propellor stirrer, all materials including the antioxidant complex, are slowly added and stirred until uniform. The product is made to weight using purified water and stirred until uniform.

EXAMPLE 24

Skin pH Balancing Toner

|  | % w/w |
| --- | --- |
| Aqua | to 100 |
| Alcohol denat. | 7.9 |
| Butylene glycol | 2 |
| Dimethicone copolyol | 1.5 |
| Sodium lactate | 0.6 |
| Glycerin | 0.5 |
| Allantoin | 0.1 |
| Propylene glycol | 0.1 |
| Lactic acid | 0.002 |
| Preservative | q.s |
| Sodium ascorbyl phosphate | 1.5 |
| *Morus alba* | 0.0023 |
| *Panax ginseng* | 0.03 |

Method

Stage 1

Into the water, lactic acid and alcohol denat are separately added and dispersed until uniform. Using a propellor stirrer, all materials including the antioxidant complex, are slowly added and stirred until uniform. The product is made to weight using purified water and stirred until uniform.

EXAMPLE 25

Skin pH Balancing Toner

|  | % w/w |
| --- | --- |
| Aqua | to 100 |
| Alcohol denat. | 7.9 |
| Butylene glycol | 2 |
| Dimethicone copolyol | 1.5 |
| Sodium lactate | 0.6 |
| Glycerin | 0.5 |
| Allantoin | 0.1 |
| Propylene glycol | 0.1 |
| Lactic acid | 0.002 |
| Preservative | q.s |
| Magnesium ascorbyl phosphate | 1.5 |
| *Morus alba* | 0.0023 |
| *Panax ginseng* | 0.03 |

Method

Stage 1

Into the water, lactic acid and alcohol denat are separately added and dispersed until uniform. Using a propellor stirrer, all materials including the antioxidant complex, are slowly added and stirred until uniform. The product is made to weight using purified water and stirred until uniform.

EXAMPLE 26 pH Balanced Cleansing Lotion

|  | % w/w |
| --- | --- |
| Aqua | to 100 |
| Paraffinum liquidum | 14 |
| Isopropyl palmitate | 7 |
| Glyceryl stearate | 2.5 |
| PEG-100 stearate | 2.5 |
| Butylene glycol | 2 |
| Hydrogenated vegetable glycerides citrate | 2 |
| Polysorbate 60 | 0.5 |
| Sorbitan stearate | 0.5 |
| *Persea gratissima* | 0.3 |
| *Prunus persica* | 0.3 |
| Propylene glycol | 0.3 |
| Acrylates/C10–30 alkyl acrylate crosspolymer | 0.12 |
| Potassium hydroxide | 0.05 |
| Tetrasodium EDTA | 0.02 |
| *Medicago sativa* | 0.0045 |
| Preservative | q.s |
| Sodium ascorbyl phosphate | 1.5 |
| *Morus alba* | 0.023 |
| Panax ginseng | 0.03 |

Method

Stage 1

Into the water, EDTA is added and dispersed. Butylene glycol is then added and dispersed. The aqueous phase is then heated to 70° C.

Stage 2

The paraffinum liquidum, isopropyl palmitate, glyceryl stearate, PEG-100 stearate, hydrogenated vegetable glycerides citrate, polysorbate 60 and sorbitan stearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 27 pH Balanced Cleansing Lotion

|  | % w/w |
| --- | --- |
| Aqua | to 100 |
| Paraffinum liquidum | 14 |
| Isopropyl palmitate | 7 |
| Glyceryl stearate | 2.5 |
| PEG-100 stearate | 2.5 |
| Butylene glycol | 2 |
| Hydrogenated vegetable glycerides citrate | 2 |
| Polysorbate 60 | 0.5 |
| Sorbitan stearate | 0.5 |
| *Persea gratissima* | 0.3 |
| *Prunus persica* | 0.3 |
| Propylene glycol | 0.3 |
| Acrylates/C10–30 alkyl acrylate crosspolymer | 0.12 |
| Potassium hydroxide | 0.05 |
| Tetrasodium EDTA | 0.02 |
| *Medicago sativa* | 0.0045 |
| Preservative | q.s |
| Magnesium ascorbyl phosphate | 1.5 |
| *Morus alba* | 0.023 |
| Panax ginseng | 0.03 |

Method

Stage 1

Into the water, EDTA is added and dispersed. Butylene glycol is then added and dispersed. The aqueous phase is then heated to 70° C.

Stage 2

The paraffinum liquidum, isopropyl palmitate, glyceryl stearate, PEG-100 stearate, hydrogenated vegetable glycerides citrate, polysorbate 60 and sorbitan stearate are mixed and heated to 70° C. to melt the waxes.

Stage 3

Using a homogeniser, stage 2 is added to stage 1 and this is mixed until emulsified and uniform. The emulsion is then cooled to below 35° C. using stirring. The remaining materials, including the antioxidant complex are then added and mixed. The product is then made to weight using purified water and is stirred until uniform.

EXAMPLE 28

Lipstick

|  | % w/w |
| --- | --- |
| *Ricinus communis* | 20 |
| Octyldodecanol | 15 |
| Pentaerylhrityl tetracaprylate/caprate | 14 |
| Mica | 10 |
| Bis-diglyceryl caprylate/caprate/isostearate/ Stearate/hydroxystearate adipate | 7.5 |
| Paraffin | 5 |
| *Cera microcristallina* | 5 |
| Propylene glycol | 2 |
| Hydrogenated castor oil | 2 |
| *Candelilla cera* | 1 |
| Carnauba | 1 |
| Synthetic wax | 1 |
| *Butyrospermum parkii* | 1 |
| Titanium dioxide | 0.5 |
| Tocopheryl acetate | 0.2 |
| Polyquaternium-37 | 0.2 |
| Red colour | q.s |
| Magnesium ascorbyl phosphate | 1.5 |
| *Morus alba* | 0.0023 |
| Panax ginseng | 0.03 |

Method

Stage 1

The antioxidant complex is pre-dispersed in propylene glycol, with stirring.

Stage 2

The remaining materials are mixed in a vessel and heated to 85° C. until melted and uniform. The product is cooled and the antioxidant complex pre-mix is added below 70° C. The product poured into a suitable container and allowed to cool to room temperature to set.

EXAMPLE 29

Lipstick

|  | % w/w |
| --- | --- |
| Ricinus communis | 20 |
| Octyldodecanol | 15 |
| Pentaerylhrityl tetracaprylate/caprate | 14 |
| Mica | 10 |
| Bis-diglyceryl caprylate/caprate/isostearate/Stearate/hydroxystearate adipate | 7.5 |
| Paraffin | 5 |
| Cera microcristallina | 5 |
| Propylene glycol | 2 |
| Hydrogenated castor oil | 2 |
| Candelilla cera | 1 |
| Carnauba | 1 |
| Synthetic wax | 1 |
| Butyrospermum parkii | 1 |
| Titanium dioxide | 0.5 |
| Tocopheryl acetate | 0.2 |
| Polyquaternium-37 | 0.2 |
| Red colour | q.s |
| Sodium ascorbyl phosphate | 1.5 |
| Morus alba | 0.0023 |
| Panax ginseng | 0.03 |

Method

Stage 1

The antioxidant complex is pre-dispersed in propylene glycol, with stirring.

Stage 2

The remaining materials are mixed in a vessel and heated to 85° C. until melted and uniform. The product is cooled and the antioxidant complex pre-mix is added below 70° C. The product poured into a suitable container and allowed to cool to room temperature to set A number of trials were conducted to demonstrate the efficacy of the synergistic combinations of antioxidant agents.

In Vitro Tests

The following procedure tests the ability of antioxidants to protect lipids form the damaging effects of UV light. The antioxidants to be tested are morus alba ("Mulberry Concentrate" from Aston Chemicals), magnesium ascorbyl phosphate and panax ginseng ("Phytexcell Panax ginseng" from Croda Chemicals Ltd). The antioxidants were tested individually at a particular concentration and in combination. In the test the antioxidant or combination of antioxidants is mixed with a known skin lipid (linoleic acid) and irradiated using UV light. The quantity of peroxides in each sample is measured colourimetrically after irradiation to assess the level of damage caused by peroxidation of the linoleic acid.

A 1% lipid stock solution is prepared dissolving linoleic in an aqueous solution of octoxynol-9 (Triton X-100). Stock solutions in aqueous TBS buffer of the following antioxidants magnesium ascorbyl phosphate, morus alba and panax ginseng were prepared at 15%, 1.0% and 1.0% respectively. In experiments where the antioxidants-were tested individually, 25 µl of the lipid stock is vortexed in an ependorf together with 5 µl of the antoxidant solution and 20 µl of Triton X~100 (mixture of water and detergent used to dissolve the lipid). In experiments where the antioxidants were tested in combination, 25 µl of the lipid stock is vortexed in an ependorf together with 5 µl of each of the antioxidant solutions and 10 µof Triton X100. The final concentration of the lipid is 0.5% and of the antioxidants is 1.5%, 0.1% and 0.1% respectively.

The control sample used in the experiment is a combination of 25 µl of the lipid stock solution and 25 µl of TritonX100 and water. This solution contains no antioxidants. Samples of this control were taken before irradiation to act as untreated controls.

Using a micropipette plate 7.5 µl of each sample is pipetted into 3 wells, i.e. in triplicate, and irradiated with UV light for 40 minutes. After irradiation an assay called the lipid peroxidation assay is carried out. This determines the amount of peroxides in each well. The reaction that occurs causes a colour change from colourless to blue which is measured colourimetrically at 675 nm. The more peroxides present the darker the blue colouration and the higher the observed absorbance.

The results showed that the amount of peroxidation present in the samples treated with the antioxidants individually is similar to that observed when no antioxidants were present whereas no peroxidation is observed when the combination of antioxidants is used. The results are shown in Table 1 below. The final column shows the percentage of peroxidation observed when compared to that seen with the irradiated controls.

TABLE 1

| UV minutes | Antioxidant | Concentration | Absorbance | |
| --- | --- | --- | --- | --- |
| 0 | | | 0 | 0 |
| 40 | | | 0.7367 | 100 |
| 40 | Magnesium ascorbyl phosphate | 1.50% | 0.84 | >100 |
| 40 | Panax ginseng | 0.10% | 0.838 | >100 |
| 40 | Morus alba | 0.10% | 0.833 | >100 |
| 40 | Combination | 1.70% | −0.119 | 0 |

No protection is seen when using the antioxidants on their own, however when in combination we see a maximum effect i.e. complete lipid protection. This is greater than the additive effect of each individual antioxidant indicating a synergistic relationship between them.

In Vivo Tests

Test formulations containing antioxidants and control formulations containing no antioxidants were applied to the skin of the forearm of volunteers. An adhesive disc is applied to the skin to sample skin cells and the disc is then irradiated with broad spectrum UVA/B to induce oxidation of the lipid. Following extraction of the lipid into methanol, the degree of lipid hydroperoxides (free radical generated damage) formed were measured colourimetrically. The degree of protection afforded by the antioxidants is thus measured and compared to unirradiated and irradiated controls.

The composition of Example 4 was given to volunteers who were instructed to use it daily on their face. The volunteers were then asked to assess how their skin felt. The skin of the volunteers noted an improvement in how moisturised their skin looked and the experts also noted improvements in skin softness and smoothness. Further improvement in the moisturised appearance of the skin was noted by the experts after 8 weeks. After 12 weeks use the experts noted that the skin of the users looked more fresh and healthy and profilomentry measurements showed that the depth of fine lines and wrinkles in the skin had been reduced.

The invention claimed is:

1. A topical cosmetic composition for application to the skin, said composition comprising a suitable diluent or carrier in combination with a synergistic mixture consisting of three anti-free-radical agents, wherein the three anti-free radical agents are
   panax ginseng, is present in an amount of 0.01 to 0.05% by weight of the composition;
   morus alba, is present in an amount of 0.001 to 0.005% by weight of the composition;
   and sodium or magnesium ascorbyl phosphate is present in an amount from 0.1 to 2% by weight of the composition.

2. The topical composition of claim 1, wherein the total amount of anti-free-radical agents present is in the range 0.5 to 2% by weight.

3. The topical composition of claim 1, wherein the total amount of anti-free-radical agents present is in the range 1 to 2% by weight.

4. The topical composition of claim 1 wherein the synergistic combination of anti-free-radicals is (a) panax ginseng, (b) morus alba and (c) sodium ascorbyl phosphate.

5. The topical composition of claim 1 wherein (a) panax ginseng is present in an amount of about 0.03% by weight of the composition; (b) the morus alba is present in an amount of about 0.0023% by weight of the composition; and (c) the sodium or magnesium ascorbyl phosphate is present in an amount from 0.15 to 1.5% by weight of the composition.

* * * * *